(12) United States Patent
Hirai

(10) Patent No.: US 10,470,463 B2
(45) Date of Patent: Nov. 12, 2019

(54) ANTIBACTERIAL PRODUCT AND METHOD OF MANUFACTURING THE SAME

(71) Applicant: Silver Future Co., Ltd., Kawaguchi-shi (JP)

(72) Inventor: Akiko Hirai, Niiza (JP)

(73) Assignee: Silver Future Co., Ltd., Kawaguchi-shi (JP)

( * ) Notice: Subject to any disclaimer, the term of this patent is extended or adjusted under 35 U.S.C. 154(b) by 0 days.

(21) Appl. No.: 15/277,624

(22) Filed: Sep. 27, 2016

(65) Prior Publication Data

US 2017/0181437 A1 Jun. 29, 2017

Related U.S. Application Data

(63) Continuation-in-part of application No. 15/135,037, filed on Apr. 21, 2016, now abandoned.

(30) Foreign Application Priority Data

| Dec. 23, 2015 | (KR) | ......................... 10-2015-0185124 |
| Apr. 21, 2016 | (KR) | ......................... 10-2016-0048677 |
| Aug. 3, 2016 | (KR) | ......................... 10-2016-0099040 |

(51) Int. Cl.
*B32B 1/02* (2006.01)
*B65D 1/02* (2006.01)
(Continued)

(52) U.S. Cl.
CPC ............... *A01N 59/16* (2013.01); *B29B 9/12* (2013.01); *B32B 1/02* (2013.01); *B32B 1/08* (2013.01);
(Continued)

(58) Field of Classification Search
CPC .... B32B 1/02; B32B 1/08; B32B 3/02; B32B 5/16; B32B 5/18; B32B 5/20; B32B 5/28;
(Continued)

(56) References Cited

U.S. PATENT DOCUMENTS

| 5,961,843 A | * | 10/1999 | Hayakawa | ............. | A01N 25/26 |
| | | | | | 210/192 |
| 2013/0216848 A1 | * | 8/2013 | Kalich | ...................... | B22F 1/02 |
| | | | | | 428/554 |

FOREIGN PATENT DOCUMENTS

| CA | 2167029 | 10/2000 |
| CN | 101530633 A | 9/2009 |

(Continued)

OTHER PUBLICATIONS

Extended European Search Report dated Jun. 2, 2017 issued in connection with related European Application No. EP 16 19 0265.
(Continued)

*Primary Examiner* — Walter Aughenbaugh

(57) ABSTRACT

Disclosed is an antibacterial product including at least one antibacterial part, wherein the antibacterial part includes a surface layer containing silver sintered under a nitrogen atmosphere or silver oxide sintered under an oxygen atmosphere. The antibacterial product prevents the proliferation of bacteria arising due to use thereof, kills bacteria, sterilizes and purifies contaminated water, and exhibits an antibacterial effect against harmful bacteria within at most 6 hr, and preferably an early antibacterial effect within 3 hr, especially 2 hr.

1 Claim, 7 Drawing Sheets

(51) Int. Cl.

| | |
|---|---|
| *A01N 59/16* | (2006.01) |
| *B29B 9/12* | (2006.01) |
| *B65D 23/02* | (2006.01) |
| *B65D 81/28* | (2006.01) |
| *B32B 5/16* | (2006.01) |
| *B32B 1/08* | (2006.01) |
| *B32B 3/02* | (2006.01) |
| *B32B 5/18* | (2006.01) |
| *B32B 5/28* | (2006.01) |
| *B32B 5/20* | (2006.01) |
| *B32B 5/30* | (2006.01) |
| *B32B 5/32* | (2006.01) |
| *B29K 23/00* | (2006.01) |
| *B29K 509/02* | (2006.01) |

(52) U.S. Cl.
CPC ............... *B32B 3/02* (2013.01); *B32B 5/16* (2013.01); *B32B 5/18* (2013.01); *B32B 5/20* (2013.01); *B32B 5/28* (2013.01); *B32B 5/30* (2013.01); *B32B 5/32* (2013.01); *B65D 1/0207* (2013.01); *B65D 1/0215* (2013.01); *B65D 23/02* (2013.01); *B65D 81/28* (2013.01); *B29K 2023/12* (2013.01); *B29K 2509/02* (2013.01)

(58) Field of Classification Search
CPC ........... B32B 5/30; B32B 5/32; B65D 1/0207; B65D 1/0215; B65D 23/02
See application file for complete search history.

(56) References Cited

FOREIGN PATENT DOCUMENTS

| | | |
|---|---|---|
| CN | 104128196 A | 11/2014 |
| EP | 2 090 672 A1 | 8/2009 |
| EP | 2 206 801 A1 | 7/2010 |
| JP | 2006-056948 A | 3/2006 |
| JP | 2006-271771 A | 10/2006 |
| JP | 2007-161498 A | 6/2007 |
| JP | 313016 U | 1/2008 |
| JP | 4130950 B2 | 8/2008 |
| KR | 20-0377167 | 3/2005 |
| KR | 10-2006-0128419 A | 12/2006 |

OTHER PUBLICATIONS

Office Action dated Sep. 20, 2018 in connection with Chinese Patent Application No. 201610885789.2 including English language translation.

* cited by examiner

ANTIBACTERIAL PRODUCT AND METHOD OF MANUFACTURING THE SAME

CROSS-REFERENCE TO RELATED APPLICATIONS

This application is a continuation-in-part of U.S. Ser. No. 15/135,037, filed Apr. 21, 2016, and claims priority of Korean Patent Applications Nos. KR 10-2016-0099040, filed Aug. 3, 2016, KR 10-2016-0048677, filed Apr. 21, 2016, and KR 10-2015-0185124, filed Dec. 23, 2015, the content of each of which is hereby incorporated by reference into the application.

BACKGROUND OF THE INVENTION

1. Technical Field

The present invention relates to an antibacterial product and a method of manufacturing the same.

2. Description of the Related Art

Typical food containers, for example, portable containers for water and beverages, such as vacuum bottles and water bottles, are known to have a drawback in that various bacteria or oral bacteria (such as *Streptococcus mutans*), which arise from contamination of a portion coming into contact with the lips of a user or the saliva of the user, or which are adhered to the fingers, are mixed with the water in the water bottle or are adhered to the water bottle when the user drinks water from the water bottle, thereby allowing various bacteria to proliferate in the water bottle. Further, it has been pointed out that there is a risk of attachment of harmful food-poisoning bacteria such as *E. coli*, or *Streptococcus mutans*, to the water bottle, or of allowing putrefactive bacteria to proliferate in the water bottle. Water bottles having an effective function of preventing bacteria from proliferating, or of killing and eliminating bacteria, have not yet been released to date.

The main reason is considered to be that, since a conventional heat-retaining vacuum water bottle mainly contains hot water at high temperatures and the main function of the vacuum water bottle is to minimize the reduction in temperature over time, it is mistakenly believed that various bacteria have difficulty surviving in the hot water contained in the water bottle, and that the sanitation of the water in the water bottle is thus maintained.

However, when the temperature of the water is reduced to a temperature of water that is capable of being drunk by humans, especially a temperature lower than body temperature, bacteria actively proliferate. Recently, beverages including sport drinks are more frequently stored at room temperature or at cold temperatures than at hot temperatures, depending on the season, and thus the contamination of the liquid in containers by bacteria has attracted attention, and symptoms such as diarrhea have occurred.

Particularly, children frequently drink beverages from the same bottle, and thus problems related to the contamination of water by, for example, *Streptococcus mutans* in the bottle are increasing. Accordingly, there is increased expectation of the development of a water bottle having water purification and water quality maintaining functions.

On one hand, containers for storing meat or fish are useful, and are mostly large-sized and the number thereof is already large. In particular, there are many cases where a considerable amount of meat or fish is stored in water. Further, the case where such food is allowed to stand in the state of being contaminated with food-poisoning bacteria is difficult to recognize or prevent. This problem is regarded as very important in terms of food hygiene, like the water-related problem of the bottle.

On the other hand, a plastic plate, when used as a kitchen board, which is a food preparation tool useful in the kitchen of every household and is usually used to cut food to be cooked, is problematic in terms of maintaining the hygiene thereof because *E. coli* and the like may be adhered to the surface thereof. With the goal of solving this problem, an antibacterial kitchen board realized by adding a plastic material with an antibacterial agent is currently sold, but desired antibacterial performance may be difficult to realize merely by the simple addition of an antibacterial agent.

Even when such an antibacterial agent is added, particles thereof are physically distributed in the plastic after the molding process, and most of the particles are not exposed to the surface of the plastic. This is considered to be due to a physical phenomenon in which a molten plastic, having low resistance, occupies the mold contact surface upon moving while coming into contact with the surface of the mold. Hence, non-plastic particles are confined inside the molten plastic, thus making it substantially impossible to expose heterogeneous molecules contained in the plastic to the surface of the plastic under the same mass condition between the plastic and the antibacterial agent, which was proven through the antibacterial testing of Examples of the present invention.

A typical antibacterial ability test requires that an antibacterial effect be achieved within a reference time of 24 or 48 hr. However, in practice, a user is considered to expect an antibacterial effect by which harmful bacteria in a food container, including a water bottle and a vacuum bottle, are killed within at most 6 hr, preferably 3 hr, and more preferably 2 hr.

Harmful bacteria start to proliferate when they are accidentally mixed with beverages in the water bottle or the vacuum bottle, but at the same time harmful bacteria need to be prevented from proliferating, that is, they need to be killed. Furthermore, in consideration of the period ranging from the time at which the container is filled with a beverage to the initiation of drinking or to the completion of drinking, a reference time of 24 hr is very long from the standpoint of common sense, and the water in the water bottle is expected to have already been drunk within 24 hr.

Therefore, from the standpoint of common sense, the antibacterial ability needs to be confirmed in an antibacterial test in which antibacterial ability sufficient to completely kill harmful bacteria or to secure a viable cell count of 100 cells/cc or less within at most 6 hr, preferably 3 hr, and more preferably 2 hr after filling the container with water, is realized in a short time. The antibacterial function of silver has been known for a long period of time to be realized by silver oligodynamic action, activating dissolved oxygen in water that is in contact with the silver surface. The history of using silver, having this main characteristic, in dishes or to store beverages is long, and the antibacterial and bacteria-reducing functions of silver are considered to be obtained not by so-called chemicals but through active oxidation. Needless to say, silver is not at all harmful to humans, and does not affect bacteria that are beneficial to humans, for example, *Lactobacillus*, but has strong antibacterial and sterilizing effects on food-poisoning bacteria and anaerobic bacteria, which are harmful to humans, due to active oxidation of the surface thereof, and the silver oligodynamic action is known to have safe antibacterial and sterilizing effects.

Meanwhile, Korean Registered Utility Model No. 20-0377167 discloses an antibacterial silver container that resists discoloration. However, the aforementioned Korean Registered Utility Model describes only an antibacterial effect obtained after 24 hr by using nano-sized pure silver powder as a component having an antibacterial function.

In the present invention, various tests have been made in order to realize a sterilizing ability in a short time. The use of pure silver resulted in poor sterilizing ability in a short time. However, products made of silver sintered under a nitrogen atmosphere or silver oxide sintered under an oxygen atmosphere have been proven to achieve 100% sterilization within at most 6 hr, preferably 3 hr, and more preferably 2 hr.

CITATION LIST

Korean Registered Utility Model No. 20-0377167

SUMMARY OF THE INVENTION

Accordingly, the present invention has been made keeping in mind the problems encountered in the related art, and the present invention is intended to provide an antibacterial product, which may prevent the proliferation of bacteria arising due to use thereof and may kill the bacteria in a short time.

In addition, the present invention is intended to provide an antibacterial product, which may sterilize and purify water contaminated by bacteria.

In addition, the present invention is intended to provide an antibacterial product, which may exhibit an antibacterial effect within at most 6 hr, and preferably an early antibacterial effect within 3 hr, especially 2 hr.

The present invention provides an antibacterial product including at least one antibacterial part, in which the antibacterial part includes a sintered silver-containing surface layer, and the sintered silver may include silver sintered under a nitrogen atmosphere or silver oxide sintered under an oxygen atmosphere.

In the present invention, the silver sintered under a nitrogen atmosphere may conceptually include a silver coating sintered under a nitrogen atmosphere.

In the present invention, the silver oxide may conceptually include a silver coating sintered in air or under an oxygen atmosphere.

In the present invention, pure silver may conceptually include a pure silver coating sintered in a vacuum.

In the present invention, sintering under an oxygen atmosphere means that 15.0% or more of the total volume of gas is oxygen. Since 20.0% or more of oxygen is contained in air, sintering in air indicates sintering under an oxygen atmosphere according to the present invention.

In an embodiment of the present invention, the antibacterial product may be selected from among a dining utensil, a cooking utensil, a food container, a food preservation appliance, a medical device, a device for plants, a device for animals, and a cleaning tool.

In an embodiment of the present invention, the antibacterial part or the material for the antibacterial product may include any material selected from among metal, glass, ceramic, stone, a mineral, plastic, and mixtures thereof.

In an embodiment of the present invention, the antibacterial part may have a shape selected from among a planar shape, a spherical shape, a rod shape, a lump shape, a particle shape, a sand shape, and a shape of an antibacterial product.

In an embodiment of the present invention, the surface layer containing silver sintered under a nitrogen atmosphere or silver oxide sintered under an oxygen atmosphere may be a layer (hereinafter, referred to as a "surface layer containing silver sintered under a nitrogen atmosphere or silver oxide sintered under an oxygen atmosphere in layer form") that includes, as a substrate, silver sintered under a nitrogen atmosphere or silver oxide sintered under an oxygen atmosphere in layer form and is positioned on the surface of the antibacterial part, or may be a layer (hereinafter, referred to as a "surface layer containing silver sintered under a nitrogen atmosphere or silver oxide sintered under an oxygen atmosphere in particle form") that includes a plastic as a substrate, contains silver sintered under a nitrogen atmosphere or silver oxide sintered under an oxygen atmosphere in particle form, exposed to the surface of the substrate, or contains not only silver sintered under a nitrogen atmosphere or silver oxide sintered under an oxygen atmosphere in particle form, exposed to the surface of the substrate, but also silver sintered under a nitrogen atmosphere or silver oxide sintered under an oxygen atmosphere in particle form, dispersed in the substrate, and is positioned on the surface of the antibacterial part.

In an embodiment of the present invention, a portion or the entirety of the antibacterial part, which is positioned beneath the surface layer containing silver sintered under a nitrogen atmosphere or silver oxide sintered under an oxygen atmosphere in layer form, may be a rough surface, or a portion or the entirety of the surface layer containing silver sintered under a nitrogen atmosphere or silver oxide sintered under an oxygen atmosphere in particle form may be a rough surface.

In an embodiment of the present invention, the rough surface may be formed through sandblasting.

In an embodiment of the present invention, the thickness of the surface layer containing silver sintered under a nitrogen atmosphere or silver oxide sintered under an oxygen atmosphere in layer form may be 0.1 to 20 µm, or the thickness of the surface layer containing silver sintered under a nitrogen atmosphere or silver oxide sintered under an oxygen atmosphere in particle form may be 10 to 60 µm.

In an embodiment of the present invention, the surface layer containing silver sintered under a nitrogen atmosphere or silver oxide sintered under an oxygen atmosphere in particle form and the antibacterial part may be integrally formed.

In an embodiment of the present invention, the antibacterial part and the surface layer containing silver sintered under a nitrogen atmosphere or silver oxide sintered under an oxygen atmosphere in particle form may include 1 to 60 parts by weight of the silver sintered under a nitrogen atmosphere or silver oxide sintered under an oxygen atmosphere in particle form, based on 100 parts by weight of the plastic.

In an embodiment of the present invention, the silver sintered under a nitrogen atmosphere or silver oxide sintered under an oxygen atmosphere in particle form may include mineral particles or rock-type particles in the core thereof.

In an embodiment of the present invention, the weight ratio of the mineral particles or the rock-type particles to the silver sintered under a nitrogen atmosphere or silver oxide sintered under an oxygen atmosphere may be 100:0.1 to 10.

In addition, the present invention provides a method of manufacturing an antibacterial product including at least one antibacterial part, comprising: (1) adding and dissolving a silver salt compound powder into water or a polar organic solvent to prepare a silver salt solution, (2) applying the silver salt solution on the antibacterial part, and (3) sintering the silver salt compound applied on the antibacterial part under a nitrogen atmosphere or an oxygen atmosphere, thus forming, on the antibacterial part, a surface layer containing silver sintered under a nitrogen atmosphere or silver oxide sintered under an oxygen atmosphere in layer form.

In an embodiment of the present invention, the material for the antibacterial part may be selected from among metal, glass, ceramic, stone, a mineral, and mixtures thereof.

In an embodiment of the present invention, in the step (1), 1 to 10 parts by weight of the silver salt compound powder may be added to 100 parts by weight of the water or the polar organic solvent.

In an embodiment of the present invention, the silver salt compound may be selected from among silver carbonate, silver chlorate, silver chloride, silver chromate, silver vanadate, silver manganate, silver nitrate, silver nitrite, silver perchlorate, silver phosphate, silver acetate, and mixtures thereof.

In an embodiment of the present invention, in the third step, the sintering may be performed at a temperature of 440° C. or higher.

In an embodiment of the present invention, a rough surface may be formed on the antibacterial part before the second step, and the silver salt solution may be applied on the rough surface in the second step.

In an embodiment of the present invention, the rough surface may be formed through sandblasting.

In an embodiment of the present invention, the surface layer containing silver sintered under a nitrogen atmosphere or silver oxide sintered under an oxygen atmosphere in layer form may be formed to a thickness of 0.1 to 20 μm.

In an embodiment of the present invention, the method may further include manufacturing the antibacterial product including the antibacterial part, after the step (3).

Also, the present invention provides a method of manufacturing an antibacterial product including at least one antibacterial part, comprising: (1) adding and mixing mineral particles or rock-type particles and a silver salt compound powder with water or a polar organic solvent, and sintering the silver salt compound under a nitrogen atmosphere or an oxygen atmosphere, thus preparing silver sintered under a nitrogen atmosphere or silver oxide sintered under an oxygen atmosphere in particle form having mineral particles or rock-type particles in the core thereof; (2) mixing and heating a plastic material and the silver sintered under a nitrogen atmosphere or silver oxide sintered under an oxygen atmosphere in particle form, thus making pellets; (3) molding the antibacterial part from the pellets; and (4) subjecting the antibacterial part to sandblasting, thus exposing the silver sintered under a nitrogen atmosphere or silver oxide sintered under an oxygen atmosphere in particle form to the surface of the antibacterial part.

In an embodiment of the present invention, in the step (1), the weight ratio of the mineral particles or rock-type particles to the silver salt compound powder may be 100:0.1 to 10, and the weight ratio of the mixture, comprising the mineral particles or rock-type particles and the silver salt compound powder, to the water or the polar organic solvent may be 1 to 70:100.

In an embodiment of the present invention, the silver salt compound may be selected from among silver carbonate, silver chlorate, silver chloride, silver chromate, silver vanadate, silver manganate, silver nitrate, silver nitrite, silver perchlorate, silver phosphate, silver acetate, and mixtures thereof.

In an embodiment of the present invention, in the step (1), the sintering may be performed at a temperature of 440° C. or higher.

In an embodiment of the present invention, in the step (2), the weight ratio of the plastic material to the silver sintered under a nitrogen atmosphere or silver oxide sintered under an oxygen atmosphere in particle form may be 100:1 to 60.

In addition, the present invention provides an antibacterial metal scrubber, manufactured by (1) adding and dissolving 1 to 10 parts by weight of a silver salt compound powder into 100 parts by weight of water or a polar organic solvent to prepare a silver salt solution, (2) immersing a metal scrubber made of metal fibers in the silver salt solution so that the silver salt solution is applied on a portion or the entirety of the surface of the fibers of the metal scrubber, and (3) sintering the silver salt compound applied on the portion or the entirety of the surface of the fibers of the metal scrubber at a temperature of 440° C. or higher under a nitrogen atmosphere or an oxygen atmosphere, thus forming, on the portion or the entirety of the surface of the fibers of the metal scrubber, a surface layer containing silver sintered under a nitrogen atmosphere or silver oxide sintered under an oxygen atmosphere.

According to the present invention, the antibacterial product can prevent the proliferation of bacteria arising due to the use thereof and can kill the bacteria, can sterilize and purify contaminated water, and can exhibit an antibacterial effect within at most 6 hr, and preferably an early antibacterial effect within 3 hr, more preferably 2 hr.

Specifically, the antibacterial product according to the present invention not only prevents contamination by bacteria arising due to the use thereof, but also has a strong ability to remove and kill harmful anaerobic bacteria, which have low resistance to active oxidation by silver, such as harmful food-poisoning bacteria, including *E. coli, Salmonella, Vibrio parahaemolyticus,* and *Staphylococcus aureus,* or *Streptococcus mutans* after a predetermined time (typically, within at most 6 hr, preferably 3 hr, and more preferably 2 hr), even when water from a river, a lake, or a swamp is placed in the antibacterial product of the invention in the event of an emergency.

DESCRIPTION OF THE SPECIFIC EMBODIMENTS

Figure 1:
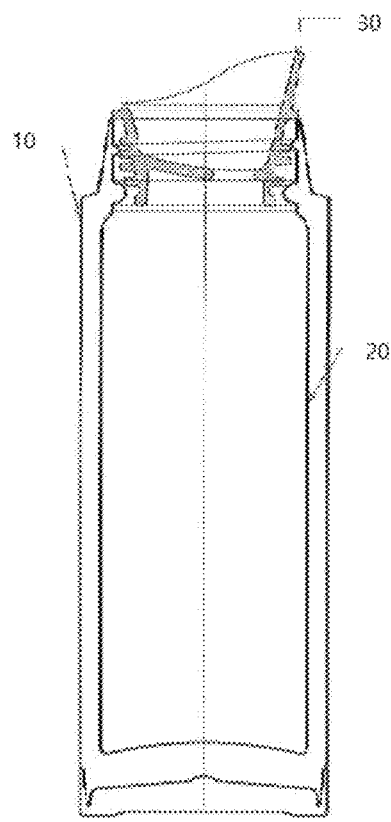
FIG. 1 is a sectional view showing a food container (a vacuum water bottle) according to an embodiment of the present invention.

Hereinafter, a detailed description will be given of embodiments of the present invention.

Antibacterial Product

According to the present invention, an antibacterial product includes at least one antibacterial part, and the antibacterial part may include a surface layer containing silver sintered under a nitrogen atmosphere or silver oxide sintered under an oxygen atmosphere.

As used herein, the term "silver sintered under a nitrogen atmosphere" is a concept including a silver coating sintered under a nitrogen atmosphere.

As used herein, the term "silver oxide" is a concept including a silver coating sintered under air or under an oxygen atmosphere.

As used herein, the term "pure silver" is a concept including a pure silver coating sintered in a vacuum.

In the present invention, sintering under an oxygen atmosphere means that 15.0% or more of the total volume of gas is oxygen. Since air comprises 20.0% or more of oxygen, sintering under air means sintering under an oxygen atmosphere according to the present invention.

The antibacterial product requires antibacterial performance, and examples thereof include dining utensils, cooking utensils, food containers, food preservation appliances, medical devices, devices for plants, devices for animals, and cleaning tools. Also, the antibacterial product, which is a product coming into contact with water or a product including water, may include, without limitation, a wide range of products requiring sanitation.

The dining utensils are used on a dining table, and examples thereof may include plates, mugs, forks, spoons, chopsticks, spoon and/or chopstick rests, pot stands, trays, spoon holders, etc.

The cooking utensils are used in cooking, and examples thereof may include mixing bowls, ladles, tongs, spatulas, wicker trays, baskets, turners, molds for rice rolls and/or rice balls, openers, cooking nets, whisks, squeezers, funnels, noodle makers, pans, pots, kitchen boards, fry pans, cutting tools (knives, scissors, etc.), kettles, tea pots, confectionery goods (shaping frames, etc.), bakery goods (bread frames, etc.), etc.

The food containers are used to receive food, and examples thereof may include single- or double-layered (vacuum) bottles, cups, tumblers, kettles, jars, packed containers, electric pots, water bottles, food trays, food storage containers, etc.

The food preservation appliances are used to preserve food in homes, restaurants, companies, etc., other than the aforementioned food containers, and specific shapes thereof are not limited, and examples thereof may include water storage tools (water tanks, water purifiers, etc.), refrigerators, Kimchi refrigerators, freezers, etc.

The medical devices are used in the medical field, nursing field, etc. and examples thereof may include tweezers, scalpels, scissors, sterilized plates, trays, mouth openers, single- or double-layered disinfectant containers (vacuum), purifiers, Ringer's solution holders, etc.

The devices for plants are used to cultivate, store, or transport plants, and examples thereof may include flowerpots, plant cultivation devices, plant storage devices, plant transport devices, etc.

The devices for animals are used to grow, store, or transport animals, and examples thereof may include fish basins, water tanks, tank decoration supplies, aquarium filters, tank cleaning supplies, oxygen supply for water tanks, motors for water tanks, live fish transport vessels, trays for pets, water bottles or thermoses for pets, food or water dispensers for pets, feed storage containers, etc.

The cleaning tools are used to remove dirt and bacteria from various products, including the aforementioned antibacterial products, using a cleaning solution such as water or detergent, and examples thereof may include a scrubber, a sponge, a brush, cloth, etc.

The antibacterial part is configured to include a component (an antibacterial component) for exhibiting antibacterial performance on the surface thereof or the surface and inside thereof. For the food container, the antibacterial part may be a portion or the entirety of each of the inner wall, bottom, lip contact part, water contact part, handle thereof and the like, or may be an entire food container. For the dining utensil, cooking utensil or food preservation appliance, the antibacterial part may be a portion or the entirety of each of the food contact part, water contact part, handle thereof and the like, or may be an entire dining utensil, cooking utensil or food preservation appliance. For the medical device, the antibacterial part may be a portion or the entirety of each of the part that contacts the body of a patient, water contact part, handle thereof and the like, or may be an entire medical device. For the device for plants, the antibacterial part may be a portion or the entirety of each of the inner wall, bottom, plant contact part, water contact part, handle thereof and the like, or may be an entire device for plants. For the device for animals, the antibacterial part may be a portion or the entirety of each of the inner wall, bottom, animal contact part, water contact part, handle thereof and the like, or may be an entire device for animals. For the cleaning tool, the antibacterial part may be a portion or the entirety of the part thereof that comes into contact with water, dirt, bacteria and the like, or may be an entire cleaning tool.

The antibacterial part may be provided in the form of a planar shape (a circular plate, a rectangular plate, or a cylindrical plate), a spherical shape, a rod shape, a lump shape, a particle shape, a sand shape, or a shape of an antibacterial product.

In an embodiment of the present invention, the antibacterial part or the material for the antibacterial product may include any material selected from among metal (rustproof metal), glass, ceramic (ceramic ware), stone, a mineral, plastic, and mixtures thereof.

Examples of the plastic include a thermoplastic resin, which is shaped by inserting a component in a hot molten state in a frame, or a thermosetting resin, which is shaped by mixing, heating, and curing components. Specific examples include, but are not limited to, polyester, polyethylene terephthalate, polyethylene, high-density or low-density polyethylene, polyvinyl chloride, polypropylene, polystyrene, impact-resistant polystyrene, polyamide, acrylonitrile butadiene styrene, polycarbonate, polyurethane, maleimide, a urea resin, a Bakelite resin, a melamine resin, melamine formaldehyde, a phenolic resin, polyepoxide, polyetherimide, polyimide, polylactic acid, polymethyl methacrylate, furan, silicone, and polysulfone, which may be used alone or in combinations of two or more.

The surface layer containing silver sintered under a nitrogen atmosphere or silver oxide sintered under an oxygen atmosphere may be a layer (hereinafter, referred to as a "surface layer containing silver sintered under a nitrogen atmosphere or silver oxide sintered under an oxygen atmosphere in layer form") that includes, as a substrate, silver sintered under a nitrogen atmosphere or silver oxide sintered under an oxygen atmosphere in layer form and is positioned on the surface of the antibacterial part.

The surface layer containing silver sintered under a nitrogen atmosphere or silver oxide sintered under an oxygen atmosphere may be a layer (hereinafter, referred to as a "surface layer containing silver sintered under a nitrogen atmosphere or silver oxide sintered under an oxygen atmosphere in particle form") that includes a plastic as a substrate, contains silver sintered under a nitrogen atmosphere or silver oxide sintered under an oxygen atmosphere in particle form, exposed to the surface of the substrate, or contains not only silver sintered under a nitrogen atmosphere or silver oxide sintered under an oxygen atmosphere in particle form, exposed to the surface of the substrate, but also silver sintered under a nitrogen atmosphere or silver oxide sintered under an oxygen atmosphere in particle form, dispersed in the substrate, and is positioned on the surface of the antibacterial part. Exposing the silver sintered under a nitrogen atmosphere or silver oxide sintered under an oxygen atmosphere in particle form to the surface of the substrate means that when the antibacterial product is exemplified by a food container, the silver sintered under a nitrogen atmosphere or silver oxide sintered under an oxygen atmosphere in particle form may come into direct contact with the food or the lips (including the organs around the lips and the hand-related organs).

In an embodiment of the present invention, a portion or the entirety of the antibacterial part, which is positioned beneath the surface layer containing silver sintered under a nitrogen atmosphere or silver oxide sintered under an oxygen atmosphere in layer form, may be a rough surface. In the case where such a rough surface is provided, the strength of adhesion of the surface layer containing silver sintered under a nitrogen atmosphere or silver oxide sintered under an oxygen atmosphere in layer form may be enhanced, and the antibacterial effect may be increased by virtue of the surface layer containing silver sintered under a nitrogen atmosphere or silver oxide sintered under an oxygen atmosphere in layer form.

In an embodiment of the present invention, a portion or the entirety of the surface layer containing silver sintered under a nitrogen atmosphere or silver oxide sintered under an oxygen atmosphere in particle form may be a rough surface. In the case where such a rough surface is provided, the exposed amount of silver sintered under a nitrogen atmosphere or silver oxide sintered under an oxygen atmosphere in particle form is increased, thus improving the antibacterial effect by virtue of the surface layer containing silver sintered under a nitrogen atmosphere or silver oxide sintered under an oxygen atmosphere in particle form.

In an embodiment of the present invention, the rough surface may be formed through sandblasting. The sandblasting is a kind of spray processing, and is performed in a manner in which glass spheres, silicon, or marine sand, having a small diameter, may be sprayed on the surface of a material using air or may fall due to gravity.

In an embodiment of the present invention, the thickness of the surface layer containing silver sintered under a nitrogen atmosphere or silver oxide sintered under an oxygen atmosphere in layer form may range from 0.1 to 20 µm. Given the above thickness range, a strong antibacterial effect may result.

In an embodiment of the present invention, the thickness of the surface layer containing silver sintered under a nitrogen atmosphere or silver oxide sintered under an oxygen atmosphere in particle form may range from 10 to 60 µm. Given the above thickness range, a strong antibacterial effect may result.

In the surface layer containing silver sintered under a nitrogen atmosphere or silver oxide sintered under an oxygen atmosphere in layer form according to an embodiment of the present invention, the silver sintered under a nitrogen atmosphere or silver oxide sintered under an oxygen atmosphere is included in an amount of 50 to 100 wt %, preferably 70 to 100 wt %, and more preferably 90 to 100 wt %, based on the total weight of the surface layer containing silver sintered under a nitrogen atmosphere or silver oxide sintered under an oxygen atmosphere in layer form. When the amount of the silver sintered under a nitrogen atmosphere or silver oxide sintered under an oxygen atmosphere, which is included in the surface layer containing silver sintered under a nitrogen atmosphere or silver oxide sintered under an oxygen atmosphere in layer form, falls within any one of the above ranges, a strong early antibacterial effect may result. When the amount of the silver sintered under a nitrogen atmosphere or silver oxide sintered under an oxygen atmosphere, which is included in the surface layer containing silver sintered under a nitrogen atmosphere or silver oxide sintered under an oxygen atmosphere in layer form, is less than 100 wt %, a silver compound such as silver or silver oxide and other impurities may be included, and additional antibacterial components may be further included, in addition to the silver compound.

In the surface layer containing silver sintered under a nitrogen atmosphere or silver oxide sintered under an oxygen atmosphere in particle form according to an embodiment of the present invention, the silver sintered under a nitrogen atmosphere or silver oxide sintered under an oxygen atmosphere is included in an amount of 1 to 60 parts by weight, and preferably 1 to 40 parts by weight, based on 100 parts by weight of the plastic. When the amount of the silver sintered under a nitrogen atmosphere or silver oxide sintered under an oxygen atmosphere, which is included in the surface layer containing silver sintered under a nitrogen atmosphere or silver oxide sintered under an oxygen atmosphere in particle form, falls within any one of the above ranges, a strong early antibacterial effect may result. In the surface layer containing silver sintered under a nitrogen atmosphere or silver oxide sintered under an oxygen atmosphere in particle form, a silver compound such as silver or silver oxide and other impurities may be included, and additional antibacterial components may be further included, in addition to the silver compound.

In an embodiment of the present invention, the silver sintered under a nitrogen atmosphere or silver oxide sintered under an oxygen atmosphere in particle form, which is exposed to the surface of the substrate or is dispersed in the substrate of the surface layer containing silver sintered under a nitrogen atmosphere or silver oxide sintered under an oxygen atmosphere in particle form, may include mineral particles or rock-type particles in the core thereof.

The mineral particles are harmless to human bodies, plants and/or animals, and may include element mineral particles, sulfide mineral particles, oxide mineral particles, halogen mineral particles, carbonate mineral particles, nitrate mineral particles, borate mineral particles, sulfate mineral particles, phosphate mineral particles, arsenate mineral particles, vanadate mineral particles, tungstate mineral particles, molybdate mineral particles, and silicate mineral particles, and the like, without limitation. Specific examples thereof may include talc particles, zeolite particles, silica particles, bentonite particles, mica particles, dolomite particles, etc. The talc particles may include talc powder for use as a food additive, for example, talc powder E553b (EU Authorization Number).

The rock-type particles are harmless to human bodies, plants, and/or animals, and particles of rock including at least one of the above minerals (e.g. element minerals, sulfide minerals, oxide minerals and the like) may be used without limitation, and specific examples thereof may include sand, etc.

In an embodiment of the present invention, the weight ratio of the mineral particles or rock-type particles to the silver sintered under a nitrogen atmosphere or silver oxide sintered under an oxygen atmosphere falls in the range of 100:0.1 to 10, and preferably 100:1 to 5.

In an embodiment of the present invention, the mineral particles or the rock-type particles may have a diameter of 10 to 20 μm. In the silver sintered under a nitrogen atmosphere or silver oxide sintered under an oxygen atmosphere in particle form according to an embodiment of the present invention, the thickness (a distance obtained by subtracting the radius of the mineral particles or rock-type particles from the radius ranging to the surface from the center of the silver sintered under a nitrogen atmosphere or silver oxide sintered under an oxygen atmosphere in particle form) of the silver sintered under a nitrogen atmosphere or silver oxide sintered under an oxygen atmosphere may fall in the range of 0.1 to 20 μm. Given the above range, a strong antibacterial effect may result.

The surface layer containing silver sintered under a nitrogen atmosphere or silver oxide sintered under an oxygen atmosphere is attached in a solid phase to the antibacterial part. The surface layer containing silver sintered under a nitrogen atmosphere or silver oxide sintered under an oxygen atmosphere is separately prepared and then assembled with the antibacterial part, or may be attached to the antibacterial part through physical or chemical combination. As is apparent from the manufacturing method, which will be described later, the surface layer containing silver sintered under a nitrogen atmosphere or silver oxide sintered under an oxygen atmosphere may be formed together with the antibacterial part.

In an embodiment of the present invention, the surface layer containing silver sintered under a nitrogen atmosphere or silver oxide sintered under an oxygen atmosphere in particle form may be integrally formed with the antibacterial part. Being integrally formed means, for example, that the antibacterial part and the surface layer containing silver sintered under a nitrogen atmosphere or silver oxide sintered under an oxygen atmosphere in particle form are formed as a single part in one mold or molding frame, or have the same or similar composition. In this case, they may be formed as a single part together with other parts. The integrally formed parts may include an additive, such as a flame retardant, a thermal stabilizer, a colorant, a pigment, a compatibilizer, a photo-stabilizer, an impact modifier, and an inorganic filler, in amounts of 0.1 to 5 wt % based on the total weight of the parts.

In an embodiment of the present invention, the antibacterial part and the surface layer containing silver sintered under a nitrogen atmosphere or silver oxide sintered under an oxygen atmosphere in particle form, which are integrally formed, may include the silver sintered under a nitrogen atmosphere or silver oxide sintered under an oxygen atmosphere in particle form in an amount of 1 to 60 parts by weight, and preferably 1 to 40 parts by weight, based on 100 parts by weight of the plastic. When the amount of the silver sintered under a nitrogen atmosphere or silver oxide sintered under an oxygen atmosphere in particle form falls within any one of the above ranges, a strong early antibacterial effect may be ensured, while the moldability of the plastic material is not hindered.

The antibacterial part alone may independently constitute the antibacterial product (e.g. a kitchen board). One or more antibacterial parts may be assembled or combined to constitute the antibacterial product. The antibacterial part may be integrally formed with other parts to constitute the antibacterial product, or may be assembled or combined with other parts to constitute the antibacterial product. In the case where the antibacterial parts are combined with thereof or where the antibacterial part is combined with other parts, the antibacterial parts, the antibacterial part and other parts, or other parts may be physically combined by a combination structure of protrusions and recesses or welding, etc., or may be chemically combined by an adhesive, etc., and thus may not be separated during either or both of use and disuse of the antibacterial product.

In an embodiment of the present invention, the antibacterial product may be a food container. The antibacterial part of the food container may be a portion or the entirety of each of the inner wall and/or the lip contact part of the food container. The food container according to an embodiment of the present invention may include a first surface layer containing silver sintered under a nitrogen atmosphere or silver oxide sintered under an oxygen atmosphere on a portion or the entirety of the inner wall thereof, and a second surface layer containing silver sintered under a nitrogen atmosphere or silver oxide sintered under an oxygen atmosphere on a portion or the entirety of the lip contact part thereof.

FIG. 1 is a sectional view showing a food container (a vacuum water bottle) according to an embodiment of the present invention. As shown in FIG. 1, the vacuum water bottle includes an outer bottle 10, an inner bottle 20, and a lip contact part 30. The first surface layer containing silver sintered under a nitrogen atmosphere or silver oxide sintered under an oxygen atmosphere is formed on a portion or the entirety of the inner wall of the inner bottle 20, and the second surface layer containing silver sintered under a nitrogen atmosphere or silver oxide sintered under an oxygen atmosphere is formed on a portion or the entirety of the lip contact part 30.

The food container may contain natural or processed food, and examples of the food may include, but are not limited to, liquid food such as water, beverages, yogurt, milk, juice, coffee, tea, alcoholic beverages and the like, semi-solid food such as puddings, jellies, creams and the like, solid food such as confectionery, butter, cheese, seasonings and the like, and solid-liquid mixed food such as noodles, soup, canned foods, meat, fish, etc.

In technical features of the present invention, oxygen in water, in contact with the surface of the silver under a nitrogen atmosphere or silver oxide sintered under an oxygen atmosphere, is activated, and thus anaerobic bacteria, such as E. coli, or poisonous bacteria harmful to the human body may be killed, thereby retaining the antibacterial performance of water in the food container (i.e. the water in the food container is imparted with antibacterial performance), and such features are demonstrated through the following examples. The antibacterial target is not limited only to the water in the food container but may be applied to various food preservation containers to thereby exhibit strong hygienic activity during the storage of food.

In an embodiment of the present invention, the material for the food container may include any one selected from among metal, glass, ceramic (ceramic ware), stone, a mineral, plastic, and mixtures thereof.

In an embodiment of the present invention, the food container may be selected from among a single- or double-layered (vacuum) bottle, a cup, a tumbler, a jar, a packed container, a food tray, and a food storage vessel.

The inner wall of the food container may be a portion of the food container that contacts food when the food is placed in a maximum or predetermined amount in the food container or when a user eats the food, and may mainly be the side surfaces and the bottom surface inside the food container. Furthermore, the inner wall of the food container may be a portion that does not contact the bodies of humans or non-human animals that eat the food.

The lip contact part of the food container may be a portion of the food container that directly contacts the lips and other perioral organs, for example, the teeth, gums, palate, tongue, and mucous membranes of the cheeks, or indirectly contacts mediated by means of food, saliva, etc. Furthermore, the lip contact part may be a portion that contacts not only the lips, but also other organs around the mouth, such as the nose, the philtrum, the cheeks, and the chin, or hand-related organs such as the fingers, the nails, the back of the hand, and the palm.

The description of the first and the second surface layer containing silver sintered under a nitrogen atmosphere or silver oxide sintered under an oxygen atmosphere remains the same as that of the surface layer containing silver sintered under a nitrogen atmosphere or silver oxide sintered under an oxygen atmosphere as above.

The inner wall (inner bottle) and the lip contact part may be combined to independently constitute the food container. The food container may include an outer bottle (FIG. 1), a handle, a lid, an opening and shutting device, a sensor, and a display device, in addition to the inner wall and the lip contact part.

For example, in the manner of a cup, a portion or the entirety of the lip contact part may be a portion or the entirety of the inner wall, and a portion or the entirety of the inner wall may be a portion or the entirety of the lip contact part. An inlet and an outlet for the food may be formed in the inner wall, the lip contact part (FIG. 1), or any other part.

The lip contact part and the inner wall (inner bottle) may be integrally formed, or may be provided as separate parts. When the lip contact part is provided as an independent part, the lip contact part and the inner wall may be physically combined by a combination structure of protrusions and recesses, welding, etc., or may be chemically combined using an adhesive, etc., and accordingly, the lip contact part and the inner wall may not be separated during either or both of use and disuse of the food container.

Furthermore, when the lip contact part is provided as an independent part, as shown in FIG. 1, the lip contact part may have a cylindrical shape and may have a screw thread on the outer surface thereof, and the portion of the inner wall (inner bottle) that comes into contact with the screw thread may have another screw thread corresponding to the previous screw thread of the outer surface of the lip contact part to thus facilitate the assembly or disassembly thereof.

The combination or assembly of parts other than the inner wall and the lip contact part, or the combination or assembly of the inner wall or the lip contact part and other parts may be the same as the combination or assembly of the inner wall and the lip contact part.

Method of Manufacturing Antibacterial Product

According to an embodiment of the present invention, a method of manufacturing the antibacterial product including at least one antibacterial part may include (1) adding and dissolving a silver salt compound powder into water or a polar organic solvent to prepare a silver salt solution, (2) applying the silver salt solution on the antibacterial part, and (3) sintering the silver salt compound applied on the antibacterial part under a nitrogen atmosphere or an oxygen atmosphere, thus forming, on the antibacterial part, a surface layer containing silver sintered under a nitrogen atmosphere or silver oxide sintered under an oxygen atmosphere in layer form.

For example, the method of manufacturing a food container including, as the antibacterial part, a portion or the entirety of an inner wall and a portion or the entirety of a lip contact part, may include (1) adding and dissolving a silver salt compound powder into water or a polar organic solvent to prepare a silver salt solution, (2) applying the silver salt solution on a portion or the entirety of the inner wall and a portion or the entirety of the lip contact part of the food container, and (3) sintering the silver salt compound applied on the inner wall and the lip contact part under a nitrogen atmosphere or an oxygen atmosphere, thus forming, on a portion or the entirety of the inner wall, a first surface layer containing silver sintered under a nitrogen atmosphere or silver oxide sintered under an oxygen atmosphere in layer form and, on a portion or the entirety of the lip contact part, a second surface layer containing silver sintered under a nitrogen atmosphere or silver oxide sintered under an oxygen atmosphere in layer form.

In an embodiment of the present invention, the material for the antibacterial part may include any one selected from among metal (rustproof metal), glass, ceramic (ceramic ware), stone, a mineral, and mixtures thereof. The antibacterial part may be provided in the form of a planar shape (a circular plate, a rectangular plate, or a cylindrical plate), a spherical shape, a rod shape, a lump shape, a particle shape, a sand shape, or a shape of an antibacterial product.

Examples of the polar organic solvent include, but are not limited to, tetrahydrofuran, ethyl acetate, acetone, dimethylformamide, acetonitrile, dimethyl sulfoxide, nitromethane, propylene carbonate, formic acid, butanol, isopropanol, n-propanol, ethanol, methanol, and acetic acid, which may be used alone or in combination.

In an embodiment of the present invention, 1 to 10 parts by weight of the silver salt compound powder may be added to 100 parts by weight of the water or the polar organic solvent in the step (1). Thereby, the manufactured food container may exhibit strong early antibacterial properties.

In an embodiment of the present invention, the silver salt compound may be selected from among silver carbonate, silver chlorate, silver chloride, silver chromate, silver vanadate, silver manganate, silver nitrate, silver nitrite, silver perchlorate, silver phosphate, silver acetate, and mixtures thereof.

In an embodiment of the present invention, the sintering temperature in the step (3) may be 440° C. or higher, for example, 440 to 1,000° C. The sintering temperature may depend on the type of silver salt compound and the material of the antibacterial part.

In an embodiment of the present invention, a rough surface may be formed on the antibacterial part before the step (2), and the silver salt solution may be applied on the rough surface in the step (20). Thereby, the strength of adhesion of the surface layer containing silver sintered under a nitrogen atmosphere or silver oxide sintered under an oxygen atmosphere in layer form may be enhanced, and the antibacterial effect may be increased by virtue of the surface layer containing silver sintered under a nitrogen atmosphere or silver oxide sintered under an oxygen atmosphere.

In an embodiment of the present invention, the rough surface may be formed through sandblasting.

The nitrogen atmosphere means that the atmosphere in the system (e.g. a furnace body) where the sintering process is performed includes nitrogen in an amount of 90 to 100 vol %, and preferably 95 to 100 vol %.

In an embodiment of the present invention, the surface layer containing silver sintered under a nitrogen atmosphere or silver oxide sintered under an oxygen atmosphere in layer form may be formed to a thickness of 0.1 to 20 μm.

In an embodiment of the present invention, the manufacture (e.g. combination or assembly) of the antibacterial product including at least one antibacterial part may be performed before the step (1), in which the antibacterial product may include other parts. The combination or assembly of the antibacterial parts, the antibacterial part and other parts, or other parts may be as described above.

For example, when the antibacterial product is a food container, the manufacture (e.g. combination or assembly) of the food container including the inner wall and the lip contact part may be implemented before the step (1), in which the food container may include other parts, for example, an outer bottle, a handle, a lid, an opening and shutting device, a sensor, and a display device.

In an embodiment of the present invention, the method may include a (4) reducing the temperature of the food container to room temperature, for example, 20° C., after the step (3).

In the case where the manufacture of the antibacterial product including at least one antibacterial part is performed before the step (1), the surface layer containing silver sintered under a nitrogen atmosphere or silver oxide sintered under an oxygen atmosphere in layer form may be formed excessively large in size, undesirably negating economic benefits. Also, the shape and size of the antibacterial product may vary, and it is difficult to uniformly carry out the above application and sintering processes for all antibacterial products.

To solve the above problem, a typical shape adapted for the antibacterial part of any antibacterial product may be applied. In this case, hygiene properties commonly required in antibacterial products may be maintained. Specifically, the method may include (5) manufacturing (e.g. combining or assembling) the antibacterial product including the antibacterial part, after the step (3) or 4), in which the antibacterial product, which is exemplified by a food container, may include other parts, for example, a bottom surface, an inner wall surface, a lip contact part, an outer bottle, a handle, a lid, an opening and shutting device, a sensor, and a display device.

The combination or assembly of the antibacterial parts, the combination or assembly of parts other than the antibacterial parts, or the combination or assembly of the antibacterial part and other parts are as described above. The aforementioned method enables the economical manufacture of the antibacterial product, enables the antibacterial part to be easily positioned on a desired portion of an antibacterial product having any shape, and effectively imparts the antibacterial product with disinfecting, purification and hygiene effects.

For example, the method of manufacturing the antibacterial product may include adding and dissolving a silver salt compound powder into water or a polar organic solvent to prepare a silver salt solution, subjecting the antibacterial part to sandblasting to form a rough surface, applying the silver salt solution on the rough surface, sintering the silver salt compound applied on the rough surface under a nitrogen atmosphere or an oxygen atmosphere to form, on the antibacterial part, a surface layer containing silver sintered under a nitrogen atmosphere or silver oxide sintered under an oxygen atmosphere in layer form, and combining or assembling the antibacterial part, having the surface layer containing silver sintered under a nitrogen atmosphere or silver oxide sintered under an oxygen atmosphere in layer form, with an additional antibacterial part or other parts, for example, a bottom surface, an inner wall surface, a lip contact part, an outer bottle, a handle, a lid, an opening and shutting device, a sensor, and a display device in the case of a food container.

In an embodiment of the present invention, the method may include washing the antibacterial product, or both washing and drying the antibacterial product, after the steps (3), (4) or (5).

According to an embodiment of the present invention, the method of manufacturing the antibacterial product including at least one antibacterial part may include (1) adding and dissolving 1 to 10 parts by weight of a silver salt compound powder into 100 parts by weight of water or a polar organic solvent to prepare a silver salt solution, (2) applying the silver salt solution on the antibacterial part, and (3) sintering the silver salt compound applied on the antibacterial part under a nitrogen atmosphere or an oxygen atmosphere (in air), thus forming, on the antibacterial part, a surface layer containing silver sintered under a nitrogen atmosphere or silver oxide sintered under an oxygen atmosphere in layer form.

In an embodiment of the present invention, the antibacterial product is an antibacterial metal scrubber. The method of manufacturing the antibacterial metal scrubber may include (1) adding and dissolving 1 to 10 parts by weight of a silver salt compound powder into 100 parts by weight of water or a polar organic solvent to prepare a silver salt solution, (2) immersing a metal scrubber made of metal fibers in the silver salt solution to apply the silver salt solution on a portion or the entirety of the surface of the fibers of the metal scrubber, and (3) sintering the silver salt compound applied on the portion or the entirety of the surface of the fibers of the metal scrubber at a temperature of 440° C. or higher under a nitrogen atmosphere or an oxygen atmosphere, thus forming, on the portion or the entirety of the surface of the fibers of the metal scrubber, a surface layer containing silver sintered under a nitrogen atmosphere or silver oxide sintered under an oxygen atmosphere.

An embodiment of the present invention provides an antibacterial metal scrubber, manufactured by the above method. The antibacterial metal scrubber may play a role in disinfecting water in a live fish transport vessel and a live fish breeding tank, purifying water in a human's bathing tub, and purifying and disinfecting water in a beverage container. The antibacterial metal scrubber has a large surface area in contact with water, exhibits high water permeability and air permeability to thus rapidly disinfect harmful bacteria of water in a container to be washed, and maintains heat resistance up to temperatures of 440° C. or higher.

According to an embodiment of the present invention, the method of manufacturing the antibacterial product including at least one antibacterial part may include (1) adding and mixing mineral particles or rock-type particles and a silver salt compound powder with water or a polar organic solvent and sintering the silver salt compound under a nitrogen atmosphere or an oxygen atmosphere, thus preparing silver sintered under a nitrogen atmosphere or silver oxide sintered under an oxygen atmosphere in particle form having the mineral particles or the rock-type particles in the core thereof; (2) mixing a plastic material with the silver sintered under a nitrogen atmosphere or silver oxide sintered under an oxygen atmosphere in particle form and heating the mixture, thus making pellets; (3) molding the antibacterial part from the pellets; and (4) subjecting the antibacterial part to sandblasting, thus exposing the silver sintered under a nitrogen atmosphere or silver oxide sintered under an oxygen atmosphere in particle form to the surface of the antibacterial part.

For example, the method of manufacturing a food container including an inner wall and a lip contact part may include (1) adding and mixing mineral particles or rock-type particles and a silver salt compound powder with water or a polar organic solvent and sintering the silver salt compound under a nitrogen atmosphere or an oxygen atmosphere, thus preparing silver sintered under a nitrogen atmosphere or silver oxide sintered under an oxygen atmosphere in particle form having the mineral particles or the rock-type particles in the core thereof; (2) mixing a plastic material with the silver sintered under a nitrogen atmosphere or silver oxide sintered under an oxygen atmosphere in particle form and heating the mixture, thus making pellets; (3) molding the inner wall, the lip contact part, or both the inner wall and the lip contact part, from the pellets; and (4) subjecting a portion or the entirety of the inner wall, a portion or the entirety of the lip contact part, or both a portion or the entirety of the inner wall and a portion or the entirety of the lip contact part to sandblasting, thus exposing the silver sintered under a nitrogen atmosphere or silver oxide sintered under an oxygen atmosphere in particle form to the surface of the inner wall, the lip contact part, or both the inner wall and the lip contact part.

Examples of the polar organic solvent include, but are not limited to, tetrahydrofuran, ethyl acetate, acetone, dimethylformamide, acetonitrile, dimethyl sulfoxide, nitromethane, propylene carbonate, formic acid, butanol, isopropanol, n-propanol, ethanol, methanol, and acetic acid, which may be used alone or in combination.

The mineral particles are harmless to human bodies, plants and/or animals, and may include element mineral particles, sulfide mineral particles, oxide mineral particles, halogen mineral particles, carbonate mineral particles, nitrate mineral particles, borate mineral particles, sulfate mineral particles, phosphate mineral particles, arsenate mineral particles, vanadate mineral particles, tungstate mineral particles, molybdate mineral particles, and silicate mineral particles, without limitation. Specific examples thereof may include talc particles, zeolite particles, silica particles, bentonite particles, mica particles, dolomite particles, etc. The talc particles may include talc powder for use as a food additive, for example, talc powder E553b (EU Authorization Number).

The rock-type particles are harmless to human bodies, plants, and/or animals, and particles of rock including at least one of the above minerals (e.g. element minerals, sulfide minerals, oxide minerals and the like) may be used without limitation, and specific examples thereof may include sand, etc.

In an embodiment of the present invention, the mineral particles or the rock-type particles may have a diameter of 10 to 20 μm. In the silver sintered under a nitrogen atmosphere or silver oxide sintered under an oxygen atmosphere in particle form according to an embodiment of the present invention, the thickness (a distance obtained by subtracting the radius of the mineral particles or rock-type particles from the radius ranging to the surface from the center of sintered silver in particle form) of the silver sintered under a nitrogen atmosphere or silver oxide sintered under an oxygen atmosphere may fall in the range of 0.1 to 20 μm. Given the above range, a strong antibacterial effect may result.

In an embodiment of the present invention, the silver salt compound may be selected from among silver carbonate, silver chlorate, silver chloride, silver chromate, silver vanadate, silver manganate, silver nitrate, silver nitrite, silver perchlorate, silver phosphate, silver acetate, and mixtures thereof.

In an embodiment of the present invention, the weight ratio of the mineral particles or the rock-type particles to the silver salt compound powder in the step (1) falls in the range of 100:0.1 to 10, and preferably 100:1 to 5. The weight ratio of the mixture, comprising the mineral particles or rock-type particles and the silver salt compound powder, to the water or polar organic solvent may fall in the range of 1 to 70:100. In this case, the manufactured antibacterial product may exhibit strong early antibacterial properties.

The nitrogen atmosphere means that the atmosphere in the system (e.g. a furnace body) where the sintering process is performed includes nitrogen in an amount of 90 to 100 vol %, and preferably 95 to 100 vol %.

In an embodiment of the present invention, the sintering temperature in the step (1) may be 440° C. or higher, for example, 440 to 1,000° C. The sintering temperature may depend on the type of silver salt compound and the kind of mineral particles or rock-type particles.

In the step (2), the weight ratio of the plastic material to the silver sintered under a nitrogen atmosphere or silver oxide sintered under an oxygen atmosphere in particle form falls in the range of 100:1 to 60, and preferably 100:1 to 40. When the weight ratio of the plastic material to the silver sintered under a nitrogen atmosphere or silver oxide sintered under an oxygen atmosphere in particle form falls within any one of the above ranges, strong early antibacterial properties of the antibacterial product including the antibacterial part may be ensured, while the moldability of the plastic material is not hindered.

In the step (2), the antibacterial part may be molded in the form of a planar shape (a circular plate, a rectangular plate, or a cylindrical plate), a spherical shape, a rod shape, a lump shape, a particle shape, a sand shape, or a shape of an antibacterial product.

In an embodiment of the present invention, the step (2) may include molding the antibacterial product including the antibacterial part from the pellets. In this case, the antibacterial part and other parts may be integrally formed.

In an embodiment of the present invention, the method may include reducing the temperature of the silver sintered under a nitrogen atmosphere or silver oxide sintered under an oxygen atmosphere in particle form to room temperature, for example, 20° C., after the step (1).

By virtue of the step (4), there may be provided a layer which includes a plastic as the substrate, contains the silver sintered under a nitrogen atmosphere or silver oxide sintered under an oxygen atmosphere in particle form, exposed to the surface of the substrate, or contains both the silver sintered under a nitrogen atmosphere or silver oxide sintered under an oxygen atmosphere in particle form, exposed to the surface of the substrate, and the silver sintered under a nitrogen atmosphere or silver oxide sintered under an oxygen atmosphere in particle form, dispersed in the substrate, and is positioned on the surface of the antibacterial part, that is, a surface layer containing silver sintered under a nitrogen atmosphere or silver oxide sintered under an oxygen atmosphere in particle form.

In an embodiment of the present invention, the method may include (5) manufacturing (e.g. combining or assembling) the antibacterial product including the antibacterial part after the step (4), in which the antibacterial product may include other parts. The combination or assembly of the antibacterial parts, the combination or assembly of parts other than the antibacterial part, or the combination or assembly of the antibacterial part and other parts are as described above.

For example, when the antibacterial product is a food container, in the step (5) manufacturing (e.g. combining or assembling) the food container including the inner wall and the lip contact part may be performed after the step (4), and the food container may include other parts, for example, an outer bottle, a handle, a lid, an opening and shutting device, a sensor, and a display device. The combination or assembly of the inner wall and the lip contact part, the combination or assembly of parts other than the inner wall and the lip contact part, or the combination or assembly of the inner wall or the lip contact part and other parts are as described above.

In an embodiment of the present invention, the method may include washing the food container or washing and drying the food container after the step (5).

According to an embodiment of the present invention, the method of manufacturing the antibacterial product including at least one antibacterial part may include (1) adding and mixing mineral particles or rock-type particles and a silver salt compound powder with water or a polar organic solvent and sintering the silver salt compound under a nitrogen atmosphere or an oxygen atmosphere (under air), thus preparing silver sintered under a nitrogen atmosphere or silver oxide sintered under an oxygen atmosphere in particle form; (2) mixing a plastic material with the silver sintered under a nitrogen atmosphere or silver oxide sintered under an oxygen atmosphere in particle form and heating the mixture, thus manufacturing pellets; (3) molding the antibacterial part from the pellets; and (4) subjecting the antibacterial part to sandblasting, thus exposing the silver sintered under a nitrogen atmosphere or silver oxide sintered under an oxygen atmosphere in particle form to the surface of the antibacterial part.

EXAMPLES

A better understanding of the present invention may be obtained through the following examples which are set forth to illustrate, but are not to be construed to limit the scope of the present invention.

Comparative Example 1

A typical bottle made of stainless steel, including a water contact part, the inner wall of which was coated with pure silver through a vacuum sintering process, was manufactured, and the time required for the antibacterial activity of the manufactured bottle to *E. coli* was measured by Japan Food Research Laboratories.

Specimen: 200 mL of mineral water containing *E. coli* was placed in a pure silver-sintered bottle having a pure silver coating obtained through vacuum sintering, and then allowed to stand Control: 200 mL of purified water containing *E. coli* were placed in a sterilized container made of synthetic resin and then allowed to stand Counts of *E. coli* were measured over time while each specimen was maintained at 20° C. The results are shown in Table 1 below.

TABLE 1

| Test strains | Test specimen | Viable cell count (cells/mL) | | | |
| --- | --- | --- | --- | --- | --- |
| | | Initiation | After 1 hr | After 3 hr | After 6 hr |
| *Escherichia coli* (NBRC 3972) | Specimen | $4.2 \times 10^5$ | $2.8 \times 10^5$ | $1.8 \times 10^5$ | $6.3 \times 10^4$ |
| | Control | $4.2 \times 10^5$ | $3.3 \times 10^5$ | $4.4 \times 10^5$ | $4.7 \times 10^5$ |

Figure 2:
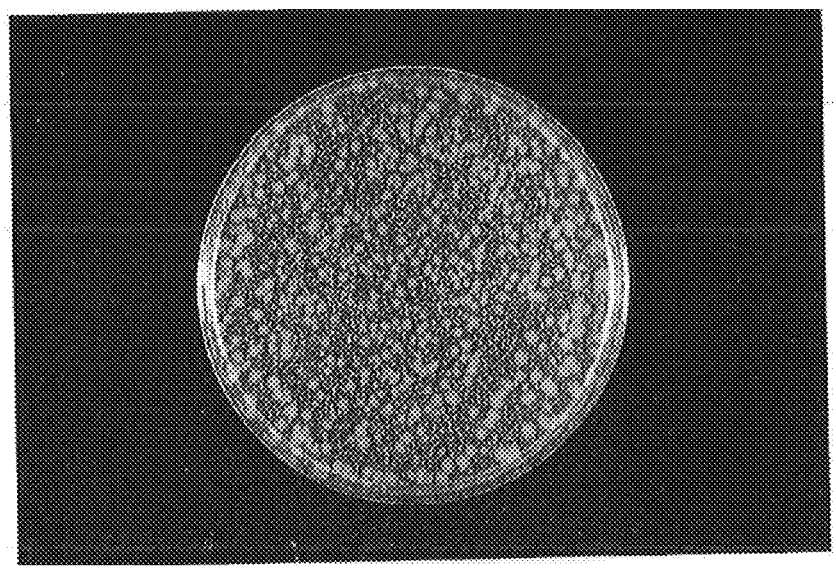
FIGS. 2, 3 and 4 are pictures showing a test solution when an antibacterial test of a pure silver-sintered vacuum bottle of Comparative Example 1 is initiated, 3 hr after the antibacterial test is performed, and 6 hr after the antibacterial test is performed, respectively.
Figure 3:
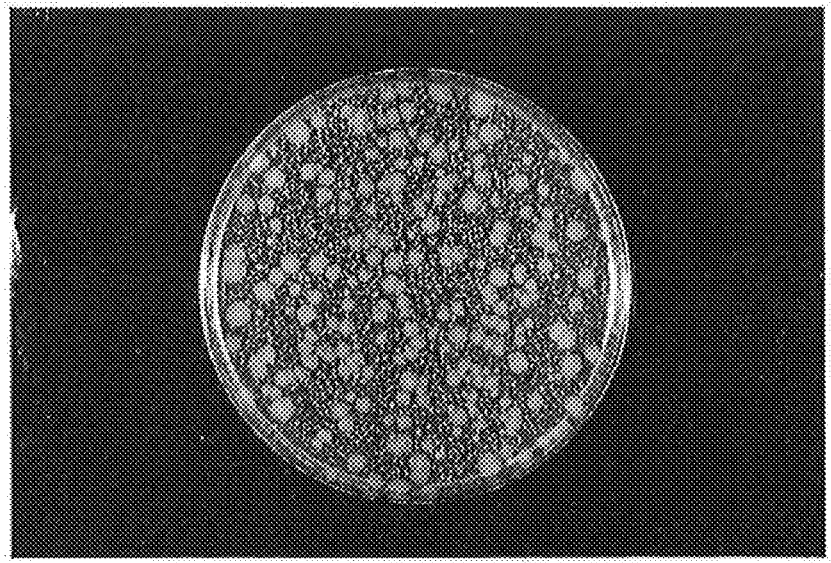
Figure 4:
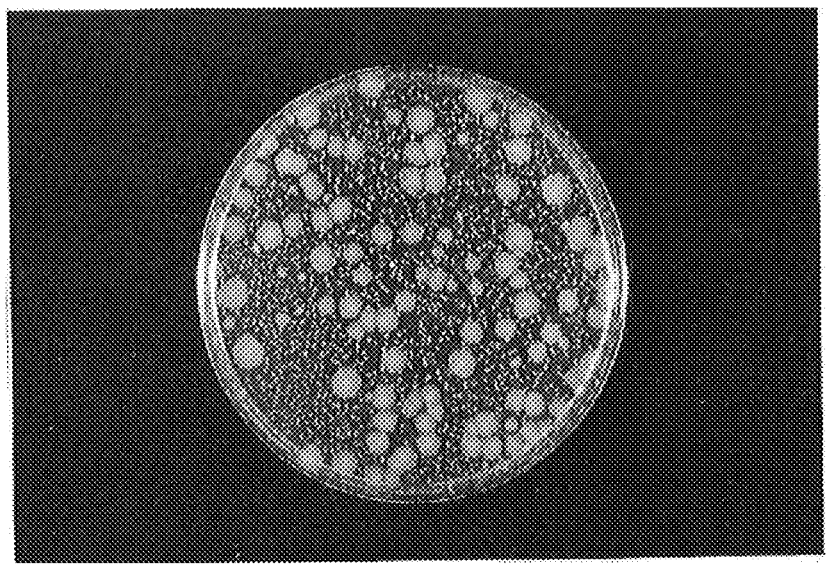

0.1 mL of the test solution was sampled and then photographed at the time of initiation, after 3 hr, and after 6 hr, and the pictures are shown in FIGS. 2, 3, and 4.

As is apparent from Table 1 and FIG. 4, very little *E. coli* was killed, even 6 hr after mineral water containing *E. coli* was placed in the pure silver-sintered bottle of Comparative Example 1.

Example 1

As shown in FIG. 1, a cylindrical food container (height: 20 cm and diameter: 5 cm), which included an inner wall (made of stainless steel) having a screw threaded upper portion, an outer bottle (made of stainless steel), a vacuum part between the inner wall and the outer bottle, and an externally screw threaded lip contact part (made of an aluminum alloy), was manufactured. 1.5 parts by weight of a silver nitrate powder was added and dissolved into 100 parts by weight of water to prepare a silver nitrate aqueous solution. The silver nitrate aqueous solution was applied on the inner wall and the lip contact part of the food container. The applied portion was sintered in air at 440° C. for 120 min, thus forming a first silver oxide-sintered surface layer on the inner wall and a second silver oxide-sintered surface layer on the lip contact part, after which the temperature was reduced to 20° C., followed by washing with water and then drying at room temperature, thereby manufacturing a bottle including the inner wall and the lip contact part on which the silver oxide-sintered surface layer was formed.

Antibacterial Test of Silver Oxide Bottle

The following antibacterial test was performed by Japan Food Research Laboratories upon request. The antibacterial ability of the manufactured silver oxide bottle to *E. coli* was tested.

Specimen 1: 200 mL of mineral water containing *E. coli* was placed in a silver oxide bottle and then allowed to stand Specimen 2: 200 mL of mineral water containing *E. coli* was placed in a silver oxide bottle, after which the silver oxide bottle was covered with a lid and then turned upside down Control: 200 mL of purified water containing *E. coli* was placed in a sterilized container made of synthetic resin, and then allowed to stand Counts of *E. coli* were measured over time while each specimen was maintained at 20° C. The results are shown in Table 2 below.

TABLE 2

| Test strains | Test specimen | Viable cell count (cells/mL) | | |
|---|---|---|---|---|
| | | Initiation | After 3 hr | After 6 hr |
| Escherichia coli (NBRC 3972) | Specimen 1 | $3.6 \times 10^5$ | $1.6 \times 10^2$ | <10 |
| | Specimen 2 | $3.6 \times 10^5$ | $2.1 \times 10^2$ | <10 |
| | Control | $3.6 \times 10^5$ | $3.6 \times 10^5$ | $4.0 \times 10^5$ |

Figure 5:
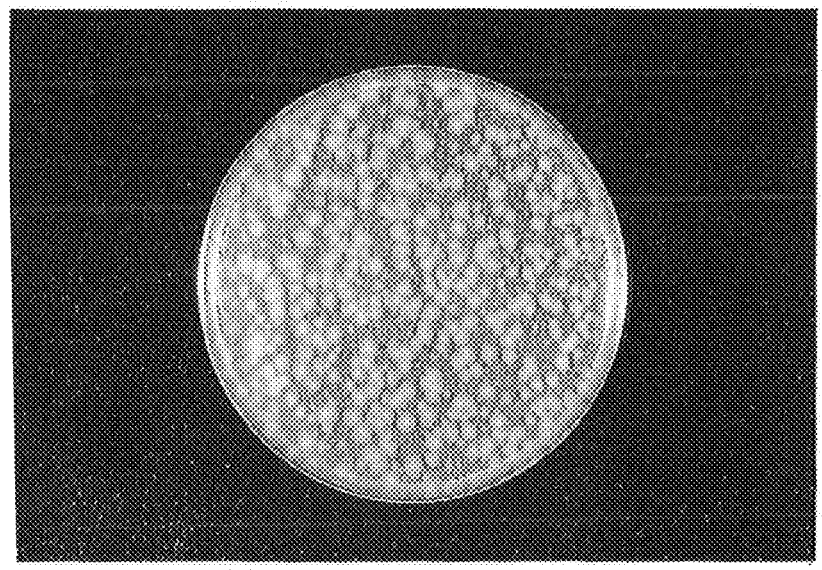
FIGS. 5, 6 and 7 are pictures showing a test solution when an antibacterial test of a silver oxide bottle of Example 1 is initiated, 3 hr after the antibacterial test is performed, and 6 hr after the antibacterial test is performed, respectively.
Figure 6:
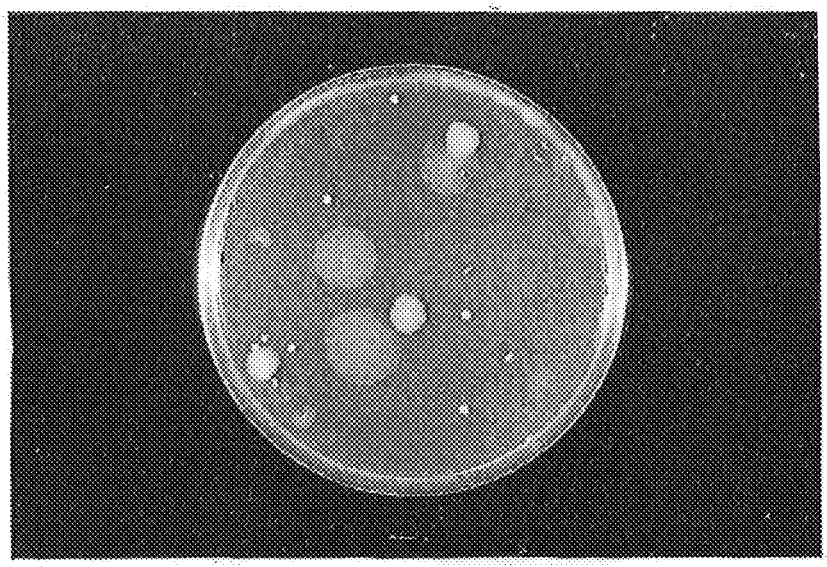

<10: Not detected 0.1 mL of the test solution was sampled and then photographed at the time of initiation, after 3 hr, and after 6 hr, and the pictures are shown in FIGS. 5, 6, and 7.

Figure 7:
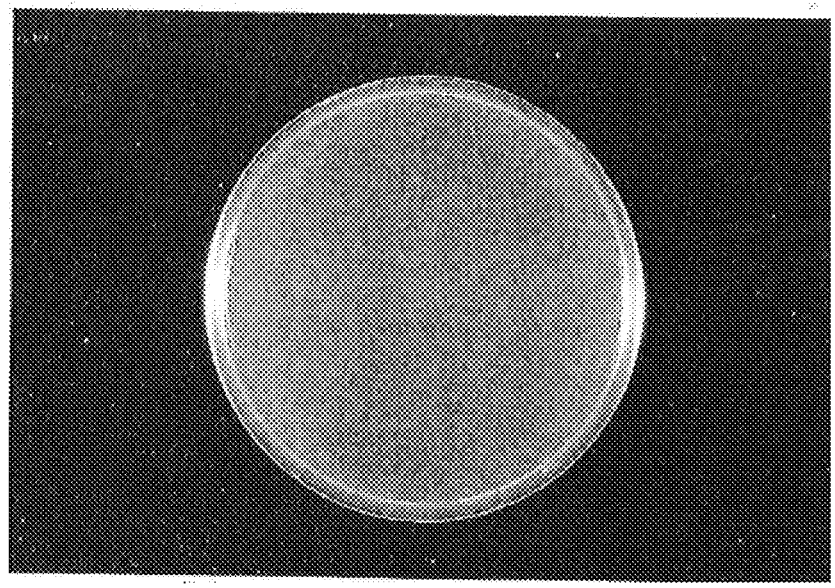
Figure 8:
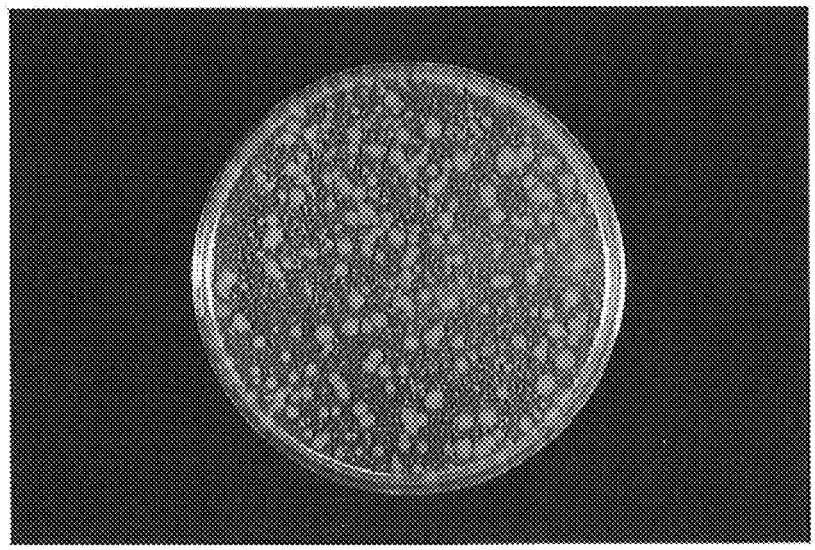
FIG. 8 is a picture showing a test solution when an antibacterial test of a silver bottle sintered under a nitrogen atmosphere and a sterilized container made of synthetic resin in Example 3 is initiated.

As is apparent from Table 2 and FIG. 7, E. coli was completely killed 6 hr after mineral water containing E. coli was placed in the silver oxide bottle.

Example 2

1000 mL of water was added with 0.5 kg of talc particles (E553b: EU Authorization Number) and 10 g of a silver nitrate powder and mixed therewith, and the mixture was dried, after which the dried powder was sintered at 440° C. for 120 min under an oxygen atmosphere (under air), thus preparing sintered silver oxide in particle form, having talc particles in the core thereof. 100 parts by weight of a plastic material (polypropylene) and 40 parts by weight of the sintered silver oxide in particle form were mixed and heated to make pellets. The pellets were used to mold a kitchen board (width: 34 cm, length: 23 cm, height: 0.3 cm). The entire upper and lower surfaces of the kitchen board were subjected to sandblasting, thus exposing the sintered silver oxide in particle form to the upper and lower surfaces of the kitchen board. The manufactured kitchen board was used as Specimen 2.

Antibacterial Test of Kitchen Board

The following antibacterial test was performed by Japan Food Research Laboratories upon request. The antibacterial ability of the following specimens to E. coli was tested.

Non-treatment 1: immediately after 200 mL of mineral water containing E. coli was sprayed on a polyethylene film Specimen 1: 200 mL of mineral water containing E. coli was sprayed on a kitchen board manufactured in the same manner as above, with the exception that sandblasting was not performed, and was then allowed to stand at 35° C. for 24 hr Specimen 2: 200 mL of mineral water containing E. coli was sprayed on a kitchen board manufactured in the same manner as above, and was then allowed to stand at 35° C. for 24 hr Non-treatment 2: 200 mL of mineral water containing E. coli was sprayed on a polyethylene film, and was then allowed to stand at 35° C. for 24 hr Counts of E. coli in each specimen were measured. The results are shown in Table 3 below.

TABLE 3

| Test strains | Measurement | Test specimen | Viable cell count/test specimen 1 cm² |
|---|---|---|---|
| Escherichia coli (NBRC 3972) | Immediately after inoculation | Non-treatment 1 | $1.1 \times 10^4$ |
| | After 24 hr at 35° C. | Specimen 1 | $1.5 \times 10^6$ |
| | | Specimen 2 | $8.3 \times 10^2$ |
| | | Non-treatment 2 | $1.5 \times 10^5$ |

As is apparent from Table 3, Specimen 2, in which the sintered silver oxide in particle form was exposed through sandblasting, was remarkably decreased in viable cell count compared to Specimen 1, in which sandblasting was not performed.

In accordance with the antibacterial activity evaluation criteria of Japan Food Research Laboratories, antibacterial activity is evaluated to be good when a difference in residual viable cell count is two digits or more, from which the kitchen board according to the embodiment of the present invention, showing a difference of three digits, is regarded as exhibiting sufficient antibacterial performance.

Example 3

As shown in FIG. 1, a cylindrical food container (height: 20 cm and diameter: 5 cm), which included an inner wall (made of stainless steel) having a screw threaded upper portion, an outer bottle (made of stainless steel), a vacuum part between the inner wall and the outer bottle, and an externally screw threaded lip contact part (made of an aluminum alloy), was manufactured. 1.5 parts by weight of a silver nitrate powder was added and dissolved into 100 parts by weight of water to prepare a silver nitrate aqueous solution. The silver nitrate aqueous solution was applied on the inner wall and the lip contact part of the food container. The applied portion was sintered at 440° C. for 120 min under a nitrogen atmosphere (99 to 100 vol % of nitrogen), thus forming a first surface layer containing silver sintered under a nitrogen atmosphere on the inner wall and a second surface layer containing silver sintered under a nitrogen atmosphere on the lip contact part, after which the temperature was reduced to 20° C., followed by washing with water and then drying at room temperature, thereby manufacturing a bottle including the inner wall and the lip contact part on which the surface layer containing silver sintered under a nitrogen atmosphere was formed.

Antibacterial Test of Silver Bottle Sintered Under a Nitrogen Atmosphere

The following antibacterial test was performed by Japan Food Research Laboratories upon request. The antibacterial ability of the manufactured silver bottle, sintered under a nitrogen atmosphere, to E. coli was tested.

Specimen: 200 mL of mineral water containing E. coli was placed in a silver bottle sintered under a nitrogen atmosphere, and then allowed to stand Control: 200 mL of purified water containing E. coli was placed in a sterilized container made of synthetic resin and then allowed to stand Counts of E. coli were measured over time while each specimen was maintained at 20° C. The results are shown in Table 4 below.

TABLE 4

| Test strains | Test specimen | Viable cell count (cells/mL) | | | |
|---|---|---|---|---|---|
| | | Initiation | After 2 hr | After 3 hr | After 4 hr |
| Escherichia coli (NBRC 3972) | Specimen | $6.4 \times 10^5$ | <10 | <10 | <10 |
| | Control | $6.4 \times 10^5$ | $6.1 \times 10^5$ | $7.0 \times 10^5$ | $7.0 \times 10^5$ |

<10: Not detected

For the specimen and the control, 0.1 mL of the test solution was sampled and then photographed at the time of initiation, after 2 hr, after 3 hr and after 4 hr, and the pictures are shown in FIGS. 8 to 14.

Figure 9:
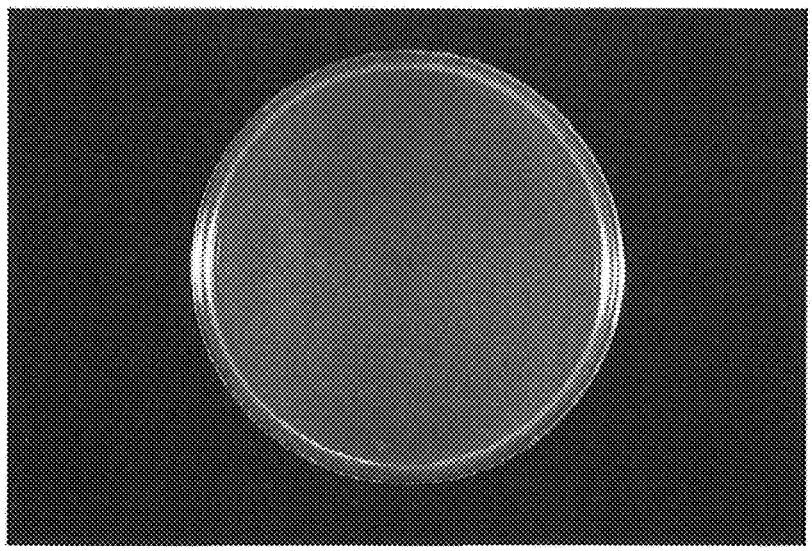
FIGS. 9, 11 and 13 are pictures showing a test solution 2 hr, 3 hr, and 4 hr, respectively, after an antibacterial test of the silver bottle sintered under a nitrogen atmosphere of Example 3 is performed.
Figure 10:
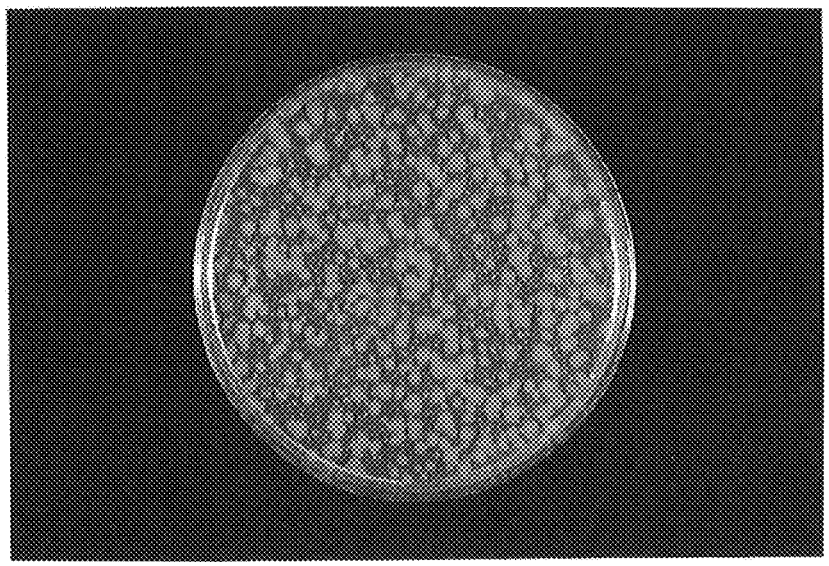
FIGS. 10, 12 and 14 are pictures showing a test solution 2 hr, 3 hr, and 4 hr, respectively, after an antibacterial test of the sterilized container made of synthetic resin in Example 3 is performed.
Figure 11:
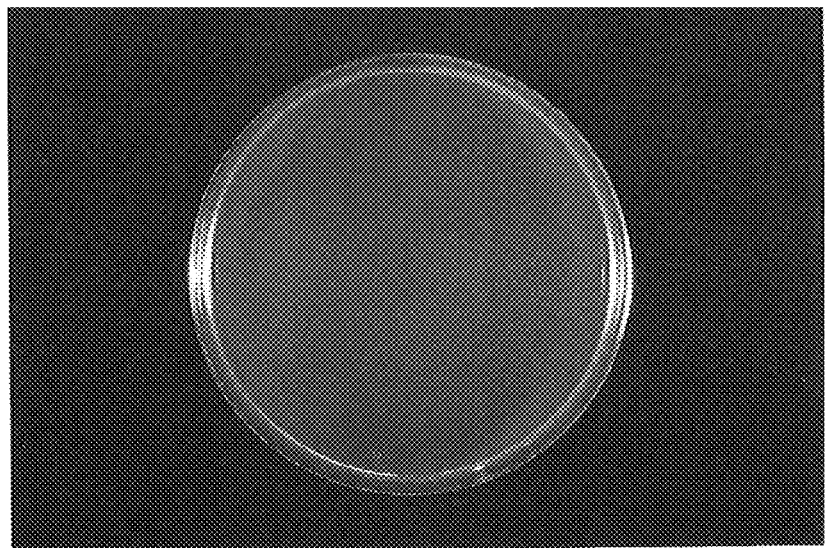
Figure 12:
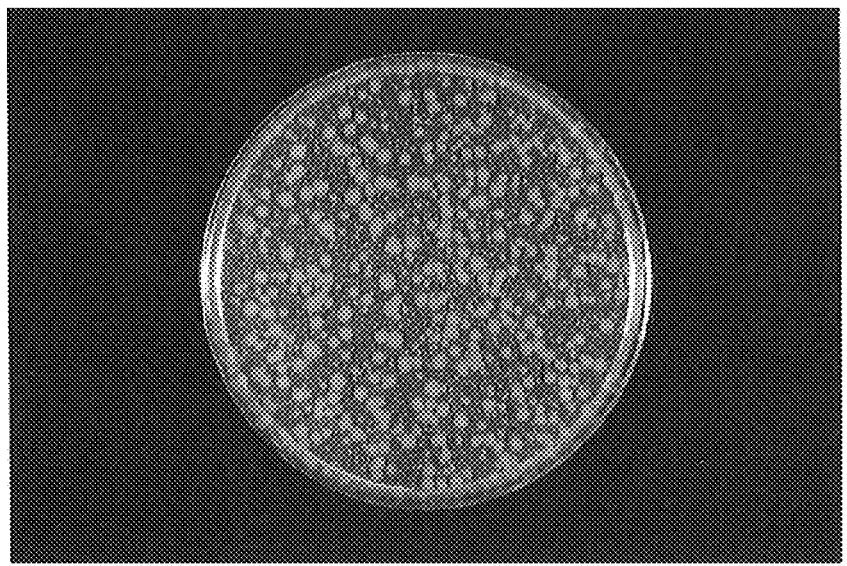
Figure 13:
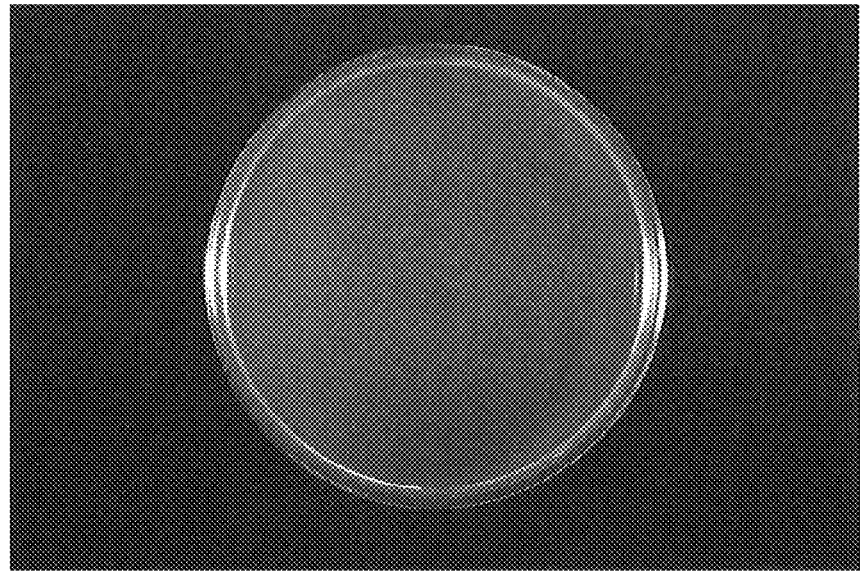
Figure 14:
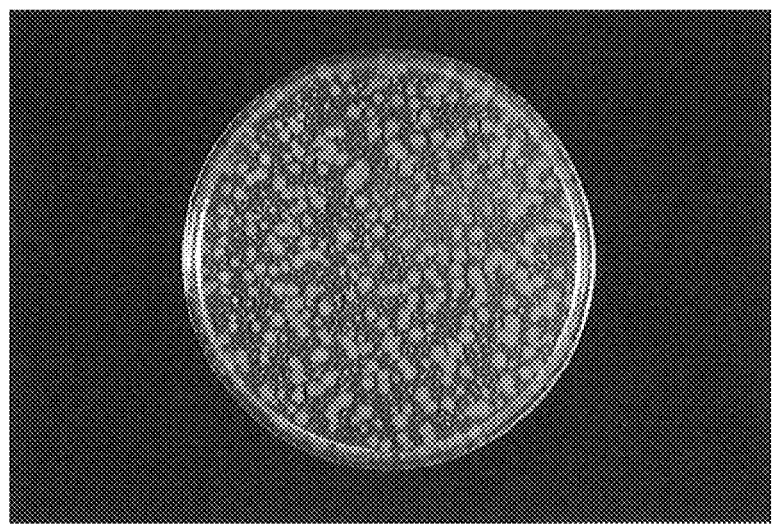

As is apparent from Table 4 and FIG. 9, *E. coli* was completely killed 2 hr after mineral water containing *E. coli* was placed in the silver bottle sintered under a nitrogen atmosphere.

Example 4

A plate made of stainless steel (10 cm×10 cm×1 cm) was manufactured. 1.5 parts by weight of a silver nitrate powder was added and dissolved into 100 parts by weight of water to prepare a silver nitrate aqueous solution. The silver nitrate aqueous solution was applied on the plate. The applied portion was sintered at 440° C. for 120 min under a nitrogen atmosphere (99 to 100 vol % of nitrogen), thus forming, on the plate, a surface layer containing silver sintered under a nitrogen atmosphere, after which the temperature was reduced to 20° C., followed by washing with water and then drying at room temperature, thereby manufacturing a plate on which the surface layer containing silver sintered under a nitrogen atmosphere was formed.

Antibacterial Test of Silver Plate Sintered in Nitrogen Atmosphere

The following antibacterial test was performed by Japan Food Research Laboratories upon request. The antibacterial ability of the manufactured silver plate sintered under a nitrogen atmosphere to *Streptococcus mutans* was tested.

Specimen: 200 mL of mineral water containing *Streptococcus mutans* was sprayed on a silver plate sintered under a nitrogen atmosphere, and then allowed to stand Non-treatment: 200 mL of purified water containing *Streptococcus mutans* was sprayed on a polyethylene film and then allowed to stand Counts of *Streptococcus mutans* were measured over time while each specimen was maintained at 35° C. The results are shown in Table 5 below.

TABLE 5

| Test strains | Measurement | Test specimen | Viable cell count/test specimen 1 cm² | | |
|---|---|---|---|---|---|
| | | | Measurement-1 | Measurement-2 | Measurement-3 |
| Streptococcus mutans | Immediately after inoculation | Non-treatment | $1.3 \times 10^4$ | $1.5 \times 10^4$ | $1.2 \times 10^4$ |
| | After 3 hr | Specimen | <0.63 | <0.63 | <0.63 |
| | | Non-treatment | $1.6 \times 10^4$ | $1.6 \times 10^4$ | $1.5 \times 10^4$ |

<0.63: Not detected

As is apparent from Table 5, *Streptococcus mutans* was completely killed 3 hr after mineral water containing *Streptococcus mutans* was sprayed on the silver plate sintered under a nitrogen atmosphere.

Consequently, based on test data from Japan Food Research Laboratories, it was confirmed that the silver bottle sintered under a nitrogen atmosphere according to the embodiment of the present invention had strong ability to remove food-poisoning bacteria (particularly, *E. coli* O-157 and O-111, *Vibrio parahaemolyticus*, *Staphylococcus aureus*, and *Salmonella*) or anaerobic bacteria such as *Streptococcus mutans*, among bacteria that are harmful to the human body. For comparison of the antibacterial performance results of the silver coatings, when the antibacterial activities of the Comparative Example, the silver oxide coating and the silver coating under a nitrogen atmosphere were compared with regard to the reduction in the time required for antibacterial action, 24 hr was shortened to 6 hr in the case of the silver oxide, and the silver coating sintered under a nitrogen atmosphere achieved desired performance within 2 hr, and thus the use of silver sintered under a nitrogen atmosphere exhibited superior results. Meanwhile, since the antibacterial effect of silver is very slowly realized on a pure silver-sintered bottle using vacuum sintering, an early antibacterial effect cannot be expected.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:
1. An antibacterial product, comprising at least one antibacterial part, wherein the antibacterial part includes a sintered silver-containing surface layer which comprises a silver salt compound sintered under a nitrogen atmosphere,
wherein the silver salt compound is selected from the group consisting of silver carbonate, silver chlorate, silver chloride, silver chromate, silver vanadate, silver manganate, silver nitrate, silver nitrite, silver perchlorate, silver phosphate, and silver acetate,
wherein the nitrogen atmosphere is 99 to 100% nitrogen by volume at 440-1000° C.,
wherein the antibacterial product is a food container, and
wherein the antibacterial part is (a) a portion or the entirety of an inner wall of the food container, (b) a lip contact part of the food container, or (c) a portion or the entirety of an inner wall of the food container and a lip contact part of the food container.

* * * * *